(12) United States Patent
Themelis (10) Patent No.: US 10,750,938 B2
(45) Date of Patent: Aug. 25, 2020

(54) METHOD, IMAGE PROCESSOR AND DEVICE FOR OBSERVING AN OBJECT CONTAINING A BOLUS OF A FLUOROPHORE

(71) Applicant: Leica Instruments (Singapore) Pte. Ltd., Singapore (SG)

(72) Inventor: George Themelis, Lindau (DE)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 117 days.

(21) Appl. No.: 15/986,001

(22) Filed: May 22, 2018

(65) Prior Publication Data

US 2018/0344137 A1     Dec. 6, 2018

(30) Foreign Application Priority Data

Jun. 1, 2017   (EP) ..................................... 17174047

(51) Int. Cl.
*G06T 7/00* (2017.01)
*A61B 1/04* (2006.01)
(Continued)

(52) U.S. Cl.
CPC .......... *A61B 1/043* (2013.01); *A61B 1/00004* (2013.01); *G06T 7/0016* (2013.01);
(Continued)

(58) Field of Classification Search
CPC ................ A61B 1/00004; A61B 1/043; A61B 2017/00066; G06T 11/001;
(Continued)

(56) References Cited

U.S. PATENT DOCUMENTS

2003/0169911 A1    9/2003  Snyder et al.
2009/0016587 A1    1/2009  Strobel et al.
(Continued)

*Primary Examiner* — Nirav G Patel
(74) *Attorney, Agent, or Firm* — Hodgson Russ LLP (57) ABSTRACT

The invention relates to a method, an image processor (26) and a medical observation device (1), such as a microscope or endoscope, for observing an object (4) containing a bolus of at least one fluorophore (12). The object (4) is preferably live tissue comprising several types (16, 18, 20) of tissue. According to the method, a set (34) of component signals (36) is provided. Each component signal (36) represents a fluorescence intensity development of the fluorophore (12) over time in a different type of tissue. A time series (8) of input frames (10) is accessed, one input frame (10) after the other. The input frames (10) represent electronically coded still images of the object (4) at subsequent time. Each input frame (10) contains at least one observation area (22) comprising at least one pixel (23). In the observation area (22) of the current input frame (10) of the time series (8), a fluorescent light intensity (I) is determined over at least one fluorescence emission wavelength (15) of the fluorophore (12). This fluorescent light intensity $(I_1)$ is joined with the fluorescence light intensities $(I_n)$ of the observation area (22) of preceding input frames (10) of the time series (8) to generate a time sequence (40) of fluorescent light intensities $(I_1, I_n)$ of the observation area (22). This time sequence (40) is decomposed on in a preferably linear combination (72) of at least some of the component signals (36) of the set (34). A new set (34) of component signals (36) is provided which includes only those component signals (36) which are present in the combination (72). An output frame (46) is generated, in which the observation area (22) is assigned a color from a color space depending on the combination (72) of component signals (36).

22 Claims, 3 Drawing Sheets

(51) Int. Cl.
   *G06T 11/00*        (2006.01)
   *A61B 1/00*         (2006.01)
   *A61B 17/00*       (2006.01)

(52) U.S. Cl.
   CPC ... *G06T 11/001* (2013.01); *A61B 2017/00066* (2013.01); *G06T 2207/10016* (2013.01); *G06T 2207/10064* (2013.01); *G06T 2207/30101* (2013.01); *G06T 2207/30104* (2013.01); *G06T 2210/41* (2013.01)

(58) Field of Classification Search
   CPC . G06T 2207/10016; G06T 2207/10064; G06T 2207/30101; G06T 2207/30104; G06T 2210/41; G06T 7/0016
   See application file for complete search history.

(56) References Cited

U.S. PATENT DOCUMENTS

2010/0053209 A1    3/2010  Rauch et al.
2011/0028850 A1    2/2011  Schuhrke et al.
2017/0293718 A1\*  10/2017  Perez ..................... G16H 30/20

\* cited by examiner

METHOD, IMAGE PROCESSOR AND DEVICE FOR OBSERVING AN OBJECT CONTAINING A BOLUS OF A FLUOROPHORE

CROSS REFERENCE TO RELATED APPLICATIONS

This application claims priority of European patent application number 17174047.5 filed Jun. 1, 2017, the entire disclosure of which is incorporated by reference herein.

FIELD OF THE INVENTION

The invention relates to a method, an image processor and a medical observation device, such as a microscope or endoscope, for observing an object, in particular live tissue, containing a bolus of at least one fluorophore.

BACKGROUND OF THE INVENTION

In neurosurgery, a fluorophore such as indocyanine green, ICG, is used to provide information related to blood flow in arteries and veins in particular of the brain. The fluorophore is injected intravenously and an NIR fluorescence imaging system, which may be part of the medical observation device, provides continuous imaging of the fluorophore's fluorescence. As the fluorophore follows the blood flow, it passes sequentially through different blood compartments, first the arteries, then the capillaries, and finally the veins. If an observation area of the object is illuminated using fluorescence excitation wavelengths which trigger the fluorescence of the fluorophore in the fluorescence emission wavelengths, the passing of the fluorophore can be observed: The fluorescence intensity in the fluorescence emission wavelengths starts to increase when the fluorophore reaches the observation area. The fluorescence intensity then increases until a maximum is reached. Thereafter, fluorescence intensity decreases due to a washout of the fluorophore and/or chemical reactions, which degrade the fluorophore.

The standard way to evaluate the blood flow using fluorescence imaging is to record a video which is replayed again and again by an observer, such as a surgeon, to observe the evolvement of fluorescence intensities in different parts of the image. Each of the three blood compartments, i.e. arteries, capillaries and veins, exhibits a maximal fluorescence intensity at a different time after the fluorophore injection. Areas without any blood flow, such as clipped vessels, do not exhibit any fluorescence at all. Thus, by watching a video sequence of the fluorescence development, an experienced observer may be able to identify the type of tissue in a specific region. This process requires experience and even for an experienced user, the identification is not reliable.

Therefore, analysis methods have been developed to automatically and reliably identify the various blood compartments. One of the approaches uses a curve-parameter extraction. This method is applied when all time frames of a video sequence are available, i.e. when the fluorescence has died off and there is no or almost no fluorophore anymore in the object. In this method, a time curve of the fluorescence intensity at a particular location is computed using all available frames. Each time curve for each pixel is analyzed to produce one or more parameters which characterize the tissue wrapped onto the respective pixel. Such parameters may be for example the arrival time of fluorescence at a certain pixel, i.e. the point in time when the fluorescence intensity at a pixel exceeds a given threshold for the first time. Another characteristic may be the peak time, i.e. the point in time when the fluorescence intensity at a pixel reaches its maximum. Other parameters such as wash-out time, maximum curve slope and curve integral can also be calculated from each curve.

Using a parameter such as the arrival time and the peak time allows a rough identification of the different blood compartments. A pseudo color image may be generated which assigns a color to a pixel depending on the arrival time. Different blood compartments exhibit different arrival times and thus can be easily distinguished using this curve parameter. For example, arrival time will be short for large arteries, as the fluorophore will reach them first. In contrast, arrival time will be later for large veins which gather blood from a large area. The visualization of the arrival time in a color-coded manner provides a still image which combines the information on the tissue gathered from the time series of frames.

Despite providing great advantages, the curve-parameter extraction method also exhibits some shortcomings. For example, it is required that the whole duration of the dynamic phenomenon is covered. The time series has to show the rise, peak, and decline of fluorescence. This means that the surgeon needs to wait for a few minutes until the analysis can be started and visualized. Moreover, several superficial tissue layers which belong to different blood compartments may be located one above the other and then lead to superimposed fluorescence time curves. In such a situation, the parameters extracted by curve-parameter extraction have a high likelihood of not bearing any physical meaning.

SUMMARY OF THE INVENTION

It is the object of the present invention to provide a method, image processor and device which do not exhibit the above shortcomings.

This object is achieved for the method mentioned initially by comprising the steps of providing a set of component signals, each component signal representing a fluorescence intensity development of the fluorophore over time, accessing a time series of input frames representing electronically coded still images of the object, each input frame containing at least one observation area, the observation area comprising at least one pixel, wherein the method further comprises the iterative process steps of automatically determining a fluorescent light intensity in the observation area of one of the input frames of the time series, the fluorescent light intensity being determined over at least one fluorescence wavelength of the fluorophore, automatically joining the fluorescent light intensity with the fluorescent light intensities of the observation area from preceding input frames of the time series to generate a time sequence of fluorescent light intensities of the observation area, automatically decomposing the time sequence into a preferably linear combination of at least some component signals of the set, automatically providing at least a subset of the component signals in the combination as a new set of component signals, and wherein an output frame is generated in which the observation area is assigned a color from a color space depending on the combination of component signals. The set of component signals and/or subset of the component signals may be generated before or during execution of the method and may be preferably stored after being generated.

For the image processor mentioned initially, this object is solved in that the image processor comprises an input section configured to receive a time series of input frames representing electronically coded still images of the object, each input frame containing at least one observation area, the observation area comprising at least one pixel, a memory section in which a set of component signals is stored, each component signal representing a fluorescence intensity development over time of the fluorophore, a computing section configured to determine the fluorescent light intensity in one input frame of the time series over at least one fluorescence emission wavelength of the fluorophore in the observation area, to join the fluorescent light intensity of the one input frame with fluorescent light intensities of previous input frames of the time series to generate a time sequence of fluorescent light intensity in the observation area, to decompose the time sequence into a preferably linear combination of the component signals in the set, and to compose a new set of component signals from at least a subset of the component signals in the combination as a replacement of the set, the image processing further comprising an image generator section configured to generate an output frame by joining at least one of the input frames of the time series with the observation area which is assigned a pseudocolor from a color space, the pseudocolor depending on the combination, and an output section configured to output the output frame.

The object is further achieved by a microscope configured to carry out the above method and/or comprising the above image processor. Further, the object is achieved by non-transitory computer storage media storing a program causing a computer to execute the above method.

The image processor may be implemented in software, hardware or in a combination of both hardware and software.

The inventive method, image processor and microscope provide several advantages over the curve-parameter extraction in the prior art.

The principle of the solution according to the invention is based on the assumption that each type of tissue exhibits typical fluorescence intensity development curves. These curves can be determined empirically. For example, if live tissue is observed, the fluorescence intensity development curves of known basic blood compartments, i.e. arteries, capillaries and veins may be measured. These (model) fluorescence intensity development curves are provided as component signals for a functional decomposition in the set. They may be generated before or during execution of the method and may preferentially be stored. As there is only a limited number of different tissues in a frame, it can be expected that actual fluorescence development curves can be represented by a limited number of the provided (model) fluorescence intensity curves.

To determine these constituent model curves, the time sequence of fluorescent light intensities in an observation area is decomposed into the various components signals. Thus, a combination of component signals in the set is computed which, when combined, results in the measured time sequence of the fluorescent light intensities, or at least, in an approximation to this time sequence.

When two or more compartments coexist in the observation area, the time sequence of the fluorescent light intensity will be a superposition, in particular a linear combination, of the individual responses of the two or more compartments to the bolus of the fluorophore, i.e. of the respective component signals. Using the decomposition, the combination of component signals will reflect the combination of the different compartments in the observation area. If, for example, there is an artery covered with capillaries in the observation area, the time sequence of fluorescent light intensities will be a superposition of the time sequence of the fluorescent light intensity of the artery and the time sequence of the fluorescent light intensity of the capillaries. As a result of the decomposition of this time sequence, the combination of component signals will be the superposition of the component signal of an artery and the component signal of capillaries.

Thus, the result of the functional decomposition of the time sequence in component signals will automatically reflect the fluorescence development characteristics of these various compartments that are superposed in the time sequence. The decomposition therefore allows identifying the different compartments in the observation area.

The functional decomposition does not need to be performed on the complete time series of input frames. The decomposition can be done by working sequentially on the input frames one at a time as they are received. Using more frames increases the accuracy of the decomposition. The decomposition may be terminated once a convergence is reached and the combination of constituent component signals does not change more than a prescribed limit.

The set of component signals which is used for the construction of the time sequence reflects the characteristics of the object in the observation area. From the combination of component signals, the prevalent type of tissue in the observation area can be determined very reliably.

The invention is not limited to the bolus of a single fluorophore, but can also be used if two or more fluorophores are used, as long as the emission wavelengths of these fluorophores are distinct so that there is no crosstalk. Then, the above-described process is simply repeated for each fluorophore. For each fluorophore a different set of component signals may be used.

Furthermore, one or more fluorophore may be degradable.

The method, image processor and microscope according to the invention can be further improved by the following features, which can be combined with each other independently and which each have a positive technical effect.

If it is desired, for example, to carry out a fast computation of the decomposition, a linear decomposition may be performed where the individual component signals are weighted and added to approximate the time sequence. This results in a set of linear equations for each observation area, for which there exist standard solutions with high computational efficiency. The selection of component signals can be done using an approximation algorithm, such as an RMS error minimization.

Preferably, each input frame represents a different state of the object at a different time. Thus, the time series of input frames records the development, i.e. built-up and wash-out of the fluorophore in the observation area over time.

An input frame, however, does not need to correspond to a single image as it is e.g. captured by a camera system, preferably a multi- or hyperspectral camera. An input frame rather may result from a combination of a plurality of still images. Such a combination can be performed by increasing contrast, such as in an HDR image, to increase the depth of the field in focus, by combining images of different layers of the object, such as in z-stacking. Further, an input frame may result from images which each are taken in different frequency bands and/or depict a different part of the object.

To reduce the computational burden, it is preferred that the iterative process steps are carried out only if the fluorescent light intensity is and/or has been above a lower fluorescence threshold in the observation area of at least one input frame. Using this approach, no computational effort is wasted for performing the iterative process steps in observation areas which are not reached by the fluorophore, or where fluorescence intensity is too weak for carrying out a reliable functional decomposition process.

Additionally, an upper fluorescence threshold may be defined, which, when exceeded, also excludes the iterative process steps to be carried out for the respective observation area. By adjustment of the upper fluorescence threshold and/or the lower fluorescence threshold respectively, the decomposition can be restricted to parts of the object, which are of special interest for the observer. An upper fluorescence threshold may be useful when the fluorescence intensity is so strong that the camera sensor is in or close to saturation.

The at least one fluorescence threshold can be constant over time or it may depend on characteristics of at least one input frame, such as brightness, contrast, color, in particular background color, fluorescence wavelength and/or a fluorescence intensity in other or all observation areas or across the input frame.

For example, the iterative process steps may be started if the fluorescence threshold is exceeded in an observation area over a predetermined number of input frames. Once such an initial threshold criterion is met, the iterative process steps may be carried out until the fluorescence intensity falls below this or another, cut-off, fluorescence threshold for a predetermined number of frames. this signals that the fluorophore has been washed out or physically or chemically degraded. If this has happened, there is no need to continue the functional decomposition.

Another or an additional cut-off condition for terminating the iterative process steps in the observation area may be convergence of the component signals in the set and/or of the weights of the component signals used in the combination. The iterative process steps may be stopped for the observation area if the change of the weights from one iterative process step to the next and/or over a predetermined number of input frames falls below a predetermined convergence threshold.

As the building of the time sequence progresses with each iterative process step, it is expected that some component signals get stronger within the combination, whereas a large number of component signals will be very weak in the combination. To converge the number of component signals used in the decomposition step, it is therefore preferred, that the number of component signals in the new set is smaller than the number of component signals in the set that has been used in the decomposition step. This reduction process can be carried out until the new set contains only a predetermined number of component signals. This predetermined number may in particular be three. This number allows assigning each component signal to one of the three blood compartments. Of course, any other number can also be used if appropriate.

According to another advantageous embodiment, the individual component signals in a combination may be weighted and a component signal may be only included in the new set of component signals that is used for the decomposition of the next input frame, if its weight in the combination exceeds a weight threshold. Using this approach eliminates the number of component signals which need to be considered in computing the approximation to the time sequence. Component signals which have a very low weight may result from noise or cross-talk such as secondary fluorescence. i.e. fluorescence induced by the fluorescence of neighboring regions. Only a predetermined number of the strongest component signals may be considered in the new set.

The weight threshold may be constant. In another approach, the number of component signals that are allowed into the new set is limited to a predetermined number. The weight threshold may also depend on input frame characteristics, such as the fluorescent light intensity of the input frame on which the iterative process steps are carried out or of a plurality of input frames.

In another embodiment, each input frame may comprise a plurality of observation areas and the iterative process steps are carried out for at least some, preferably all of the observation areas.

Independent of the actual number of observation areas in each input frame, an observation area is at a constant location within the input frames of the time series. This means that throughout the time series, the observation area comprises the same at least one pixel.

The observation areas preferably are non-overlapping and may together form the complete input frame. The input frame may consist of tiled observation areas. In a preferred embodiment, the observation area consists of a single pixel.

Another approach to weed out those component signals which may result from noise is to consider the frequency of occurrence of a component signal either in the observation area, in at least a subset of the observation areas, such as the neighboring observation areas, or all observation areas in the input frames. Only those component signals are retained in the new set that have a frequency of occurrence which exceeds a predetermined prevalence threshold. The frequency of occurrence may be measured across some or all observation areas and/or across a plurality of previous input frames.

In another preferred embodiment, the iterative process steps are carried out while input frames of the time series are received, e.g. directly from a camera system or an image processing system.

Further, it is preferred that the iterative process steps are carried out in real time. In particular, the iterative process steps may be completed between receiving two subsequent input frames of the time series. The update of the set of component signals preferably takes place at the same rate as new input frames are received. In this context, the time between receiving two subsequent input frames may correspond to a frame rate of a camera system from which the input frames are derived. Preferably, the frame rate is faster than a flicker frame rate, which is typically faster than 26 Hz. These approaches allow visualizing the result of the decomposition immediately after the fluorescence has degraded and the fluorophore been washed out or decayed.

The output frames may be generated at the same rate as the input frames so that a user can visually control the decomposition process and the adjustment of the set of component signals. This allows also monitoring in real time any unexpected and unwanted effects, such as movement of the object. The output frames may be displayed on a monitor.

If, in the output frame, each of the component signals in the set is assigned a different color, preferably a primary color, the different compartments can be distinguished visually much easier in the output frame.

In the following, the invention is further explained with reference to the accompanying drawings using an exemplary embodiment. This description is not meant to be considered limiting but serves only as an explanation. According to the above description, features having a technical effect which is not needed for a particular application may be omitted from the described embodiment in such an application. Vice versa, a feature mentioned above which is not contained in the described embodiment but has a technical effect that is of advantage for a particular application may be additionally included.

BRIEF DESCRIPTION OF THE DRAWING VIEWS

Throughout the figures, elements which are identical or similar with respect to function and/or design are assigned the same reference numeral.

In the figures.

DETAILED DESCRIPTION OF THE INVENTION

First, the invention is described with reference to FIGS. 1 and 2.

Figure 1:
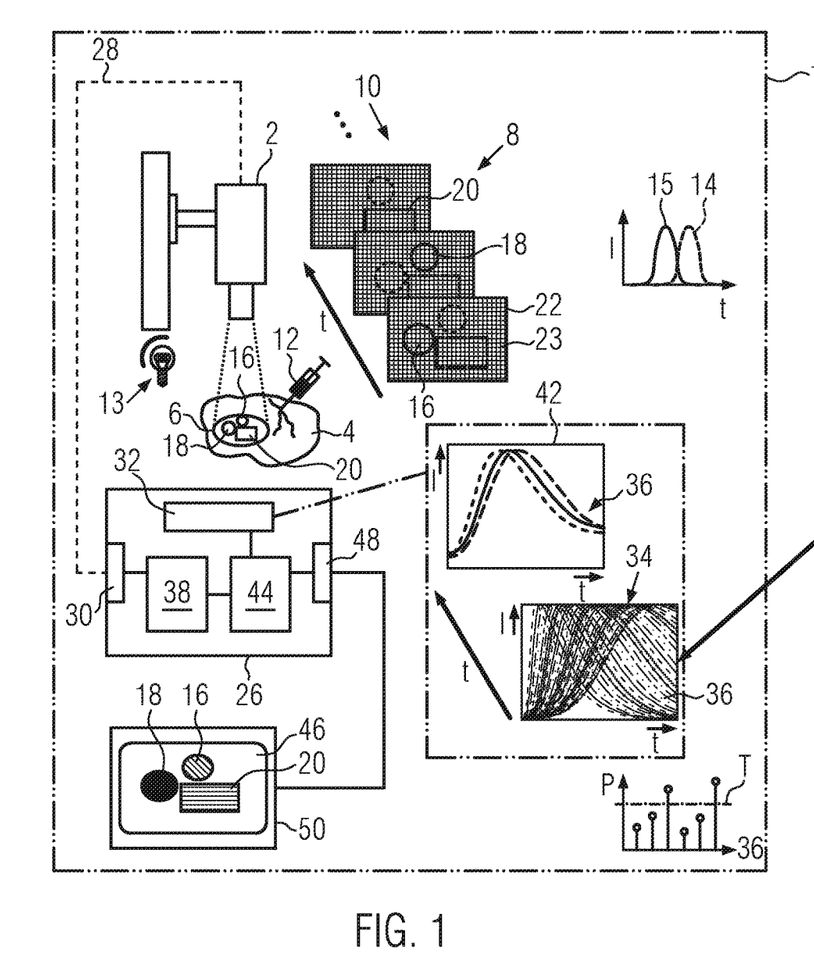
FIG. 1 shows a schematic rendition of a medical observation device according to the invention.

FIG. 1 shows a schematic representation of a medical observation device 1, such as a microscope or an endoscope. Only by way of example, a microscope shown with a camera system 2, in particular, a multi- or hyperspectral camera, which is directed onto an object 4. The camera system 2 captures a field of view 6 and records electronically coded still images that form the basis of a time series 8 of input frames 10. An input frame 10 may result from a combination of more than one electronically coded still images or from a single such image. A combination of several images can be used to increase contrast or the depth of the field of view 6, e.g. by combining pictures of different layers of the object 4 as in z-stacking. Additional or alternative combinations may comprise stitching neighboring images, combining images recorded at different wavelengths, such as a visible-light image and an NIR-image, or joining images that have been filtered differently.

The object 4 may in particular be live tissue. The object 4 has been provided with a bolus of at least one fluorophore 12 which, after application, starts to spread across the object 4. The fluorophore 12 may be degradable. An illumination system 13 illuminates at least the field of view 6 and includes fluorescence excitation wavelengths 14 that excite fluorescence of the fluorophore 12. The fluorescence of the at least one fluorophore 12 is emitted in fluorescence emission wavelengths 15 that are recorded by the camera system 2 preferably in addition to light in the visible-light range. If more than one fluorophore 12 is used, at least the emission wavelengths 15 should not overlap, so that the fluorophores 12 can be distinguished by their color.

The time series 8 of input frames 10 represents the interaction of the fluorophore 12 with the object 4 over time. In live tissue, the fluorophore 12 will reach the field of view 6 after a specific time. The intensity of the fluorescent light emitted by the fluorophore 12 will peak and then decay. The times of arrival of the fluorophore 12, of its peak and of its decay are representative for different types of tissue. Typically, three types of blood compartments, namely arterial tissue 16, capillary tissue 18 and venous tissue 20 may be differentiated. In other applications, a different number of tissues may be needed to be distinguished.

Each input frame 10 contains at least one observation area 22 which may be a single pixel 23 or a preferably connected assembly of pixels. Across the input frames 10 of a time series 8, the observation area 22 is preferably fixed in location with respect to the input frame 10.

Depending on the type of tissue 16, 18, 20 which is mapped onto the observation area 22 of the input frames 10, the fluorescent light intensity exhibits a different variation over time. This is schematically shown by the circular and rectangular areas in the input frames 10 of FIG. 1. Over time t, different areas become more visible at different times and then decay.

If there is more than one observation area 22 in the input frames 10, the observation areas 22 preferably do not overlap. It is preferred that each input frame 10 consists of observation areas 22 that are tiled to cover the complete input frame 10.

The time series 8 is analyzed by an image processor 26 which is part of the medical observation device 1 or may be used for upgrading an existing medical observation device 1. The image processor 26 is connected to the camera system 2 via a data transmission line 28 which may be wired, wireless, or a combination of both. The data transmission line 28 may be connected to an input section 30 of the image processor 26. The input section 30 is configured to receive the time series 8.

The image processor 26 further comprises a memory section 32, in which a set 34 of component signals 36 is stored. The set 34 my comprise e.g. between 10 and 200 component signals, depending on the object, the fluorophore, the lighting conditions and the computational power available.

Each component signal 36 is a discrete or analytic time curve representing the development of fluorescent light intensity I over time t in a specific type of tissue. At least one of time t and intensity I may be a dimensionless and/or normalized quantity. Each component signal 36 represents the reaction of a different type of tissue to the bolus of the at least one fluorophore 12 administered at time $t_0$. The different component signals 36 represent e.g. arterial tissue having arteries of different diameters, venous tissue having veins of different diameters and capillary tissue with capillaries of different diameters. The diameter of the respective vessels, the amount of vessels, and the flow cross section of the tissue in a specific compartment will determine the shape of the component signal 36, i.e. the time when the fluorophore 12 arrives and thus fluorescent light intensity increases, and the rate with which the fluorophore 12 is washed out from the tissue, i.e. fluorescent light intensity decreases.

Each component signal 36 may have been empirically determined by previous measurements. Different sets 34 may be used for different fluorophores and/or for different objects 4, such as different types of organs. For example, a different set 34 may be used for brain tissue and for muscle tissue.

The image processor 26 further comprises a computing section 38. The computing section 38 is configured to determine, for each observation area 22, the fluorescent light intensity I in one, current, input frame 10 of the time series 8. The fluorescent light intensity I is determined over at least one fluorescence emission wavelength 15 of the fluorophore 12 in the observation area 22. If, for example, indocyanine green is used as a fluorophore, the fluorescence wavelengths are located between 750 nm and 950 nm. The fluorescent light intensity may be determined in any part of this region and preferably includes the wavelengths between 780 nm and 850 nm where fluorescence is strongest. The fluorescent light intensity I may be computed by summing or integrating the fluorescent light intensity over several emission wavelengths 15. As a result, a fluorescent light intensity $I_1$ is obtained for the input frame 10 at time $t_1$. This fluorescent light intensity is also shown in FIG. 2 although it is not part of the set 34.

Further, the computing section 38 is configured to join the fluorescent light intensity, here $I_1$, of the current input frame 10 with the fluorescent light intensities $I_n$ of at least the previous input frames 10 of the times series 8. The fluorescent light intensities $I_n$ of the previous frames as well as the frames at a later time are also shown in FIG. 2 as dots, although, again, they are not part of the set 34. The fluorescent light intensities $I_n$ of the previous frames are surrounded by a phantom line 40 for easier identification. The computing section 38 is adapted to generate a time sequence 40 by logically joining the fluorescent light intensity $I_1$ to the previously determined fluorescent light intensities $I_n$ in the observation area 22.

The computing section 38 is further configured to decompose the time sequence 40 into a preferably linear combination of the component signals 36 in the set 34. Thus, the computing section 38 determines those component signals 36 which make up the time sequence 40 in the observation area 22. These component signals 36 are indicative of the type 16, 18, 20 of tissue which is located in the observation area 22.

The computing section 38 is further configured to compose a new set 34 of component signals 36 from at least a subset of the component signals 36 in the combination which results in the time sequence 40.

These steps are then repeated for each observation area 22 before work is started on the next input frame 10 using the new set of component signals 36.

Each observation area 22 may be assigned a separate set 34 or a single set 34 may be used for the complete input frame 10. Alternatively, a set 34 may be shared among a group of observation areas 22, wherein each input frame 10 may comprise a plurality of such groups.

At the end of this iterative process, when fluorescence has decayed in the object, a final set 42 ideally comprises only those component signals 36 which are indicative of the type 16, 18, 20 of tissue in the respective observation area 22. The weight of the component signals 36 of the final 42 set needed to build the time sequence 40 at a particular observation area 22 is indicative of the prevalence of the respective type 16, 18, 20 of tissue in the respective observation area 22.

The image processor 26 further comprises an image generator section 44 which is configured to generate an output frame 46 from at least one input frame 10 of the time series 8, preferably the input frame 10 which has just been analyzed by the computing section 38, and from the observation area 22. A pseudocolor is assigned by the image generator section 44 to the observation area 22, the pseudocolor depending on the combination of component signals 36 in the respective observation area 22, or of their weight respectively. For example, using an RGB-color space, the color red may be used for the component signal designating arterial issue, the color green for the component signal designating capillary tissue and the color blue for the component signal designating venous tissue. The color of the observation area is then determined by the mixture of red, green and blue which corresponds to the respective weights of the three component signals.

Finally, the image processor 26 may comprise an output section for outputting the output frame 46.

The medical observation device 1 may comprise a display 50, which is connected to the output section 48 and in which the output frame 46 may be displayed. In the output frame 46 in the display 50, the different pseudocolors of the type 16, 18, 20 of tissue are schematically depicted as a different filling and hatching.

Figure 3:
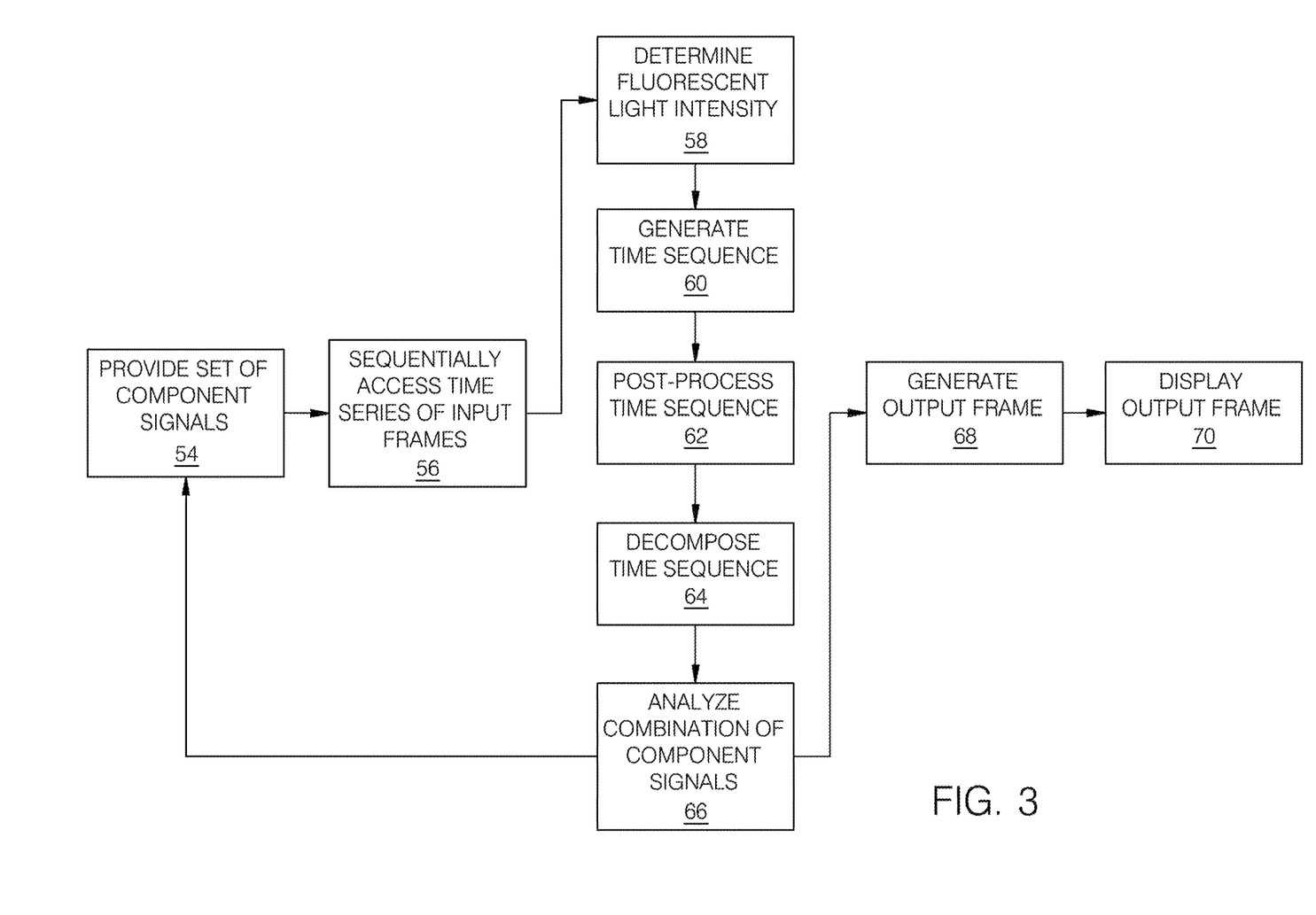
FIG. 3 shows a schematic representation of the method according to the invention.

In FIG. 3, the steps that may be carried out by the various elements of the medical observation device 1 are shown.

In a first step 54, the set 34 of component signals 36 is provided. The set 34 of component signals 36 may be generated before or during carrying out the method and may be preferentially stored.

Next, in step 56, the time series 8 of input frames 10 is accessed sequentially. This access may be performed in real time, as explained above.

In step 58, the fluorescent light intensity I in the observation area 22 is determined.

Figure 2:
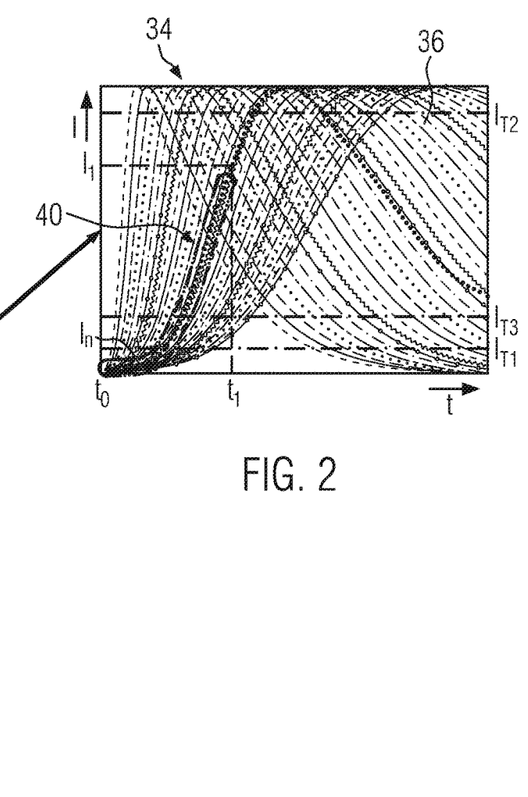
FIG. 2 shows a schematic representation of a set of component signals.

The process may, in one configuration, only proceed to the next step 60 if the fluorescent light intensity I in the observation area 22 in the current input frame 10 exceeds a lower fluorescence threshold $I_{T1}$ (FIG. 2) and/or is below an upper fluorescence intensity threshold $I_{T2}$ (FIG. 2). Once this criterion is met, the observation area 22 may undergo the iterative process until the fluorescent light intensity I in the observation area 22 falls below a decay threshold $I_{T2}$. The decay threshold $I_{T2}$ may be the same as or be higher or lower than the lower intensity threshold $I_{T1}$. A threshold may be assumed to have been passed if the intensity exceeds or falls below the threshold in a single input frame, in a predetermined number of preferably subsequent previous input frames and/or if the average fluorescent light intensity I in the observation area computed over a predetermined number of input frames falls below or exceeds the respective threshold.

If the threshold criterion with regard to $I_{T1}$ and $I_{T2}$ is met, the fluorescent light intensity $I_1$ in the current input frame 10 is joined with the fluorescent light intensities $I_n$ in the observation area 22 of the preceding input frames 10 so that the time sequence 40 is generated. The time sequence 40 may, in step 62, undergo post processing, e.g. the time sequence 40 may be smoothed, a curve-fit may be computed, normalization and/or a band- or low-pass filtering may be carried out.

In the next iterative process step 64, the time sequence 40 is decomposed into the best-fitting combination of component signals 36 of the set 34. The best fit may be computed for example using an RMS algorithm.

Steps 54 to 64 may, in one variant, be repeated for all or several observation areas 22 in the input frames 10, before the next step is performed. Alternatively, the process first goes to the next step 66 before working on another observation area 22 of the input frame 10.

In the next step 66, the combination of component signals 36 in one of the observation areas 22, some observation areas or all observation areas of the input frame 10 is analyzed. A new set 34 is composed only of those component signals 36 which are strongest in the particular combination of a single observation area 22 or in the combinations of a plurality of observation areas 22. For example, only those component signals are retained of which the weight exceeds a weight threshold. If more than one observation area is used, the average weight across a plurality of observation areas may be used. The average may also be computed over time from previous input frames. Cumulatively or alternatively, only a predefined number of the strongest component signals may be retained.

Further, only those component signals 36 may be retained in the new set, of which the frequency of occurrence P, across a plurality of observation areas 22, preferably all observation areas 22, exceeds a prevalence threshold T (FIG. 1).

The aim in this step is to reduce the number of component signals in the set 34 for the next input frame. In this step, it is assumed that component signals that are weak and/or do not occur frequently result from noise and errors.

The weight of each component signal 36 in at least the latest combination of component signals 36 of the new set 34 may be stored, e.g. in the memory section.

The set 34 which has been provided at step 54 is then replaced by the new set 34 and the process starts again with the next input frame or the next observation area 22 in the current input frame 10.

As already stated above, the method allows to maintain different sets 34 for different fluorophores 12 and/or observation areas 22. If a single set 34 is maintained for all the observation areas 22 in an input frame 10, then the number of component signals 36 will be high, as it can be expected that a variety of tissues is contained in an input frame 10. As each component signal 36 represents a different type of tissue, a larger number of component signals 36 is needed to represent the part of the object 4 which is mapped onto the input frames 10. In this case, it is the weight of the various component signals 36 in a single observation area 22 that is indicative for the type of tissue prevalent in this observation area 22. The computational effort needed for this method is comparatively low as there is only a single set 34. However, due to the large number of component signals 36 in the set 34, there is the risk that in some observation areas 22, the wrong combination of component signals 36 is computed.

This source of error can be avoided at the expense of computational effort if a plurality of sets 34 is maintained for the input frames 10. In the extreme, every observation area 22 may have its own set 34. In this case, the component signals 36 in the set 34 are indicative of the tissue types 16, 18, 20 in the respective observation area 22 and the weight of the respective component signal 36 in the combination is indicative of the prevalence of the tissue in the observation area 22.

In a balanced approach, a set of observation areas 22 may share a common set 34. Such groups of observation areas 22 may be e.g. classified by the time when the fluorescence intensity threshold $I_{T1}$ (FIG. 2) has been exceeded. By defining two or more time intervals, these groups may be easily identified.

As a further measure, a break-off or cut-off criterion may be defined for each observation area 22. When this criterion is met, the iterative process is stopped for this particular observation area 22 and the latest weights of the component signals 36 of the new set in the last combination of component signals is stored for later analysis.

Further, the output frame 46 may be generated in a step 68 and, in step 70, displayed in the display 50.

The steps 68 and 70 need not to be carried out every time the iterative process steps 58 to 66 have been computed, i.e. for every input frame 10 of the time series 8, but can be performed at predetermined time intervals. Preferably, however, the iterative process steps 58 to 66 are carried out in real time, i.e. at the same rate as the input frames 10 are received. The access to the input frames 10 at step 56 preferably occurs at a frame rate which is faster than the flicker frame rate, i.e. the frame rate which is required for a smooth rendition of a video sequence for the human eye.

Typically, the flicker frame rate is faster than 26 Hz. The output frames 46 are preferably also generated in the same frequency as the frame rate.

Of course, the process described above may also run as a batch process on a recorded video sequence.

Figure 4:
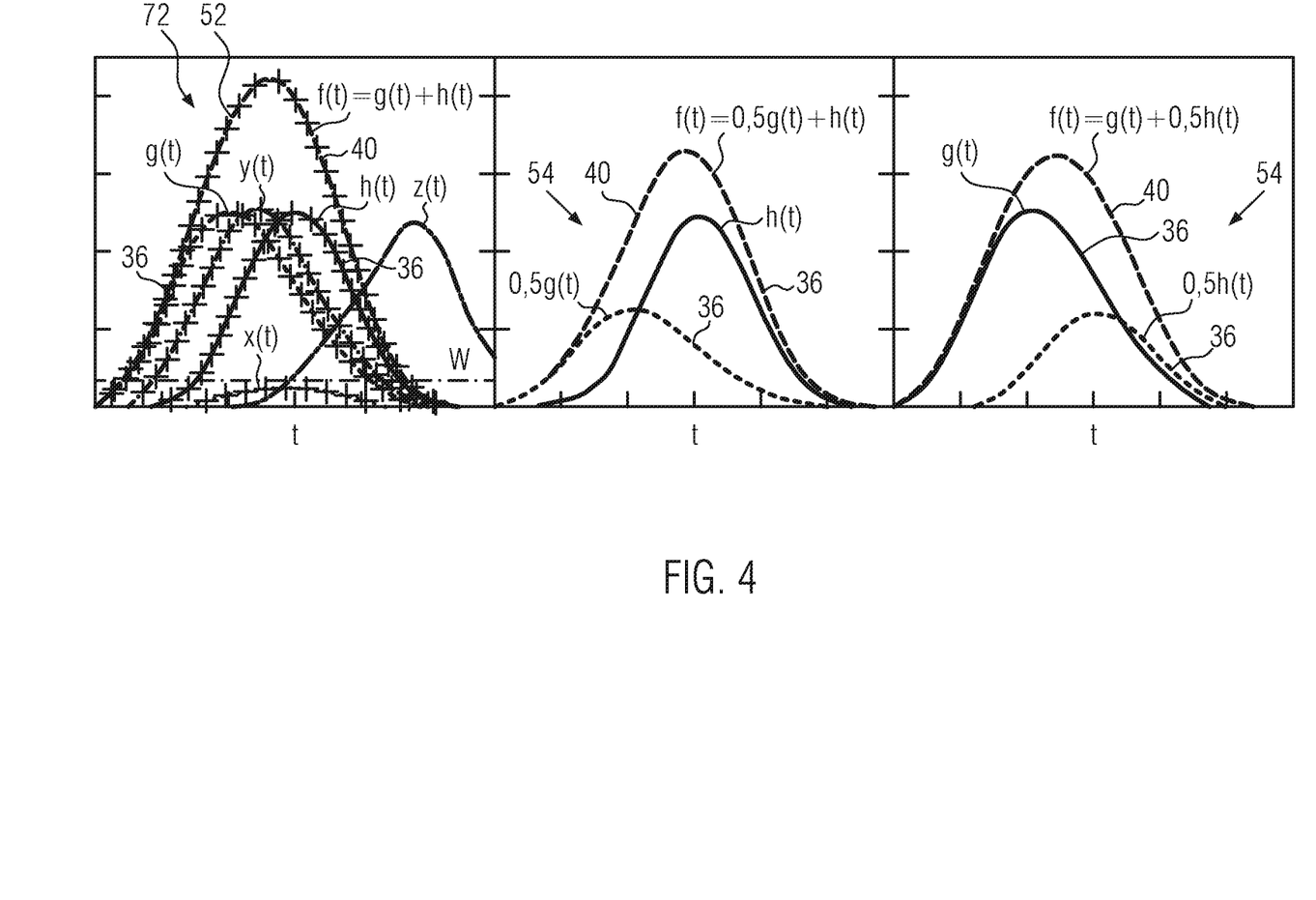
FIG. 4 shows a schematic rendition of a decomposition of a time sequence of fluorescent light intensities.

FIG. 4 illustrates the decomposing of a time sequence 40 into two or more component signals 36 which are shown as discrete-time functions g(t), h(t), x(t), y(t), z(t). The time sequence 40 can be expressed as a combination 72 of these functions.

For the functional decomposition of the time sequence 40, the closest approximation of f(t) is computed such that $$f(t) \approx a \cdot g(t) + b \cdot h(t) + c \cdot x(t) + d \cdot y(t) + e \cdot z(t)$$

holds. As the time sequence 40 consists of a plurality of sample points 52, the weights a to e can be accurately determined by various standard algorithms such as an RMS approximation. In the left-hand part of FIG. 4, the time sequence 40 is shown to have been successfully decomposed in two component signals g(t) and h(t), each having the same normalized weight e.g. a=b=1. The functions for component signals g(t) and z(t) do not contribute to the time sequence, d=e=0. the function x(t) has only a very small weight which is below a weight threshold W, c<W, and thus will be considered as resulting from noise.

In the middle part of FIG. 4, the weight of the function g(t) is half of the weight of the function h(t) in order to best approximate the function f(t). This situation is reversed in the right-hand part of FIG. 4, where the weight of the function h(t) is only half the weight of the function g(t).

REFERENCE NUMERALS 1 medical observation device
2 camera system
4 object
6 field of view
8 time series
10 input frame
12 fluorophore
13 illumination system
14 fluorescence excitation wavelengths
15 fluorescence emission wavelengths
16 arterial tissue
18 capillary tissue
20 venous tissue
22 observation area
23 pixel
26 image processor
28 data transmission line
30 input section
32 memory section
34 set of component signals
36 component signal
38 computing section
40 time sequence
42 final set of input sections
44 image generator section
46 output frame
48 output section
50 display
52 sample points
54, 56, 58, 60, 62, 64, 66, 68,70 process steps
72 combination of component signals
a, b, c, d, e weights
f, g, h, x, z, y discrete time functions
I fluorescent light intensity $I_1$ fluorescent light intensities at time $t_1$ in a specific observation area
$I_{T1}, I_{T2}, I_{T3}$ thresholds for the fluorescent light intensity
$I_n$ time sequence of fluorescent light intensities in a specific observation area over time
P frequency of occurrence of component signal
T prevalence threshold
t time
$t_0$ time of application of fluorophore to object
$t_1$ specific time
W weight threshold

What is claimed is:

1. A method for observing an object (4) containing a bolus of at least one fluorophore (12), the method comprising the steps of:
   providing a set (34) of component signals (36), each component signal (36) representing a fluorescence intensity development of the fluorophore (12) over time (t);
   accessing a time series (8) of input frames (10) representing electronically coded still images of the object (4), each input frame (10) containing at least one observation area (22), the observation area (22) comprising at least one pixel (23);
wherein the method further comprises iterative process steps of:
   automatically determining a fluorescent light intensity ($I_1$) in the observation area (22) of one of the input frames (10) of the time series (8), the fluorescent light intensity (I) being determined over at least one fluorescence emission wavelength (15) of the fluorophore (12);
   automatically joining the fluorescent light intensity ($I_1$) with respective fluorescence light intensities ($I_n$) of the observation area (22) from preceding input frames (10) of the time series (8) to generate a time sequence (40) of fluorescence light intensities ($I_1, I_n$) of the observation area (22);
   automatically decomposing the time sequence (40) into a combination (72) of at least some component signals (36) of the set (34);
   automatically providing at least a subset of the component signals (36) in the combination (72) as a new set (34) of component signals (36);
and wherein an output frame (46) is generated in which the observation area (22) is assigned a color from a color space depending on the combination (72) of component signals (36),
wherein the iterative process steps are carried out while the input frames (10) of the time series (8) are received.

2. The method according to claim 1, wherein the iterative process steps are carried out only if the fluorescent light intensity ($I_1, I_n$) is above a fluorescence threshold ($I_{T1}$) in the observation area (22) of at least one input frame (10).

3. The method according to claim 1, wherein the individual component signals (36) in the combination (72) are weighted and wherein a component signal (36) is only included in the new set (34) if the weight (a,b,c,d,e) of such component signal (36) in the combination (72) exceeds a weight threshold (W).

4. The method according to claim 1, wherein the number of component signals (36) in the new set (34) is smaller than the number in the set (34) used for the decomposition.

5. The method according to claim 1, wherein a predetermined number of the strongest component signals (36) in the combination (72) is selected to be included in the new set (34).

6. The method according to claim 1, wherein each input frame (10) comprises a plurality of observation areas (22) and wherein the iterative process steps are carried out for all of the plurality of observation areas (22).

7. The method according to claim 6, wherein the iterative process steps further comprise the step of automatically including only those component signals (36) in the set (34), of which a frequency of occurrence (P) in the observation areas (22) exceeds a prevalence threshold (T).

8. The method according to claim 1, wherein the output frames (46) are displayed on a monitor.

9. The method according to claim 1, wherein the output frames (46) are displayed in real time as the input frames (10) are received.

10. Non-transitory computer storage media storing a program causing a computer to execute the method according to claim 1.

11. A method for observing an object (4) containing a bolus of at least one fluorophore (12), the method comprising the steps of:
   providing a set (34) of component signals (36), each component signal (36) representing a fluorescence intensity development of the fluorophore (12) over time (t);
   accessing a time series (8) of input frames (10) representing electronically coded still images of the object (4), each input frame (10) containing at least one observation area (22), the observation area (22) comprising at least one pixel (23);
wherein the method further comprises iterative process steps of:
   automatically determining a fluorescent light intensity ($I_1$) in the observation area (22) of one of the input frames (10) of the time series (8), the fluorescent light intensity (I) being determined over at least one fluorescence emission wavelength (15) of the fluorophore (12);
   automatically joining the fluorescent light intensity ($I_1$) with respective fluorescence light intensities ($I_n$) of the observation area (22) from preceding input frames (10) of the time series (8) to generate a time sequence (40) of fluorescence light intensities ($I_1, I_n$) of the observation area (22);
   automatically decomposing the time sequence (40) into a combination (72) of at least some component signals (36) of the set (34);
   automatically providing at least a subset of the component signals (36) in the combination (72) as a new set (34) of component signals (36);
and wherein an output frame (46) is generated in which the observation area (22) is assigned a color from a color space depending on the combination (72) of component signals (36),
wherein the iterative process steps are carried out between receiving two subsequent input frames (10) of the times series (8).

12. The method according to claim 11, wherein the output frames (46) are displayed on a monitor.

13. The method according to claim 11, wherein the output frames (46) are displayed in real time as the input frames (10) are received.

14. Non-transitory computer storage media storing a program causing a computer to execute the method according to claim 11.

15. A method for observing an object (4) containing a bolus of at least one fluorophore (12), the method comprising the steps of:

providing a set (34) of component signals (36), each component signal (36) representing a fluorescence intensity development of the fluorophore (12) over time (t);

accessing a time series (8) of input frames (10) representing electronically coded still images of the object (4), each input frame (10) containing at least one observation area (22), the observation area (22) comprising at least one pixel (23);

wherein the method further comprises iterative process steps of:

automatically determining a fluorescent light intensity ($I_1$) in the observation area (22) of one of the input frames (10) of the time series (8), the fluorescent light intensity (I) being determined over at least one fluorescence emission wavelength (15) of the fluorophore (12);

automatically joining the fluorescent light intensity ($I_1$) with respective fluorescence light intensities ($I_n$) of the observation area (22) from preceding input frames (10) of the time series (8) to generate a time sequence (40) of fluorescence light intensities ($I_1$, $I_n$) of the observation area (22);

automatically decomposing the time sequence (40) into a combination (72) of at least some component signals (36) of the set (34);

automatically providing at least a subset of the component signals (36) in the combination (72) as a new set (34) of component signals (36);

and wherein an output frame (46) is generated in which the observation area (22) is assigned a color from a color space depending on the combination (72) of component signals (36), wherein output frames (46) are generated at the same frame rate as the input frames (10) are received.

16. The method according to claim 15, wherein the output frames (46) are displayed on a monitor.

17. The method according to claim 15, wherein the output frames (46) are displayed in real time as the input frames (10) are received.

18. Non-transitory computer storage media storing a program causing a computer to execute the method according to claim 15.

19. An image processor (26) for a medical observation device (1), the image processor (26) comprising an input section (30) configured to receive a time series (8) of input frames (10) representing electronically coded still images of the object (4), each input frame (10) containing at least one observation area (22), the observation area (22) comprising at least one pixel (23)

a memory section (32) in which a set (34) of component signals (36) is stored, a component signal (36) representing the course of fluorescence intensity of time (t) of the fluorophore (12)

a computing section (38) configured to execute iterative process steps to determine the fluorescent light intensity (I) in the observation area (22) of one input frame (10) of the time series (8) over at least one fluorescence emission wavelength (15) of the fluorophore (12) in the observation area (22), to join the fluorescent light intensity ($I_1$) of the observation area (22) of the one input frame (10) with fluorescent light intensities (I) of previous input frames (10) of the time series (8) to generate a time sequence (40) of fluorescent light intensity ($I_1$, $I_n$) in the observation area (22), to decompose the time sequence (40) into a combination (72) of the component signals (36) in the set (34), and to compose a new set (34) of component signals (36) from the component signals (36) of the combination (72) as a replacement of the set (34), wherein the iterative process steps are carried out while the input frames (10) of the time series (8) are received, an image generator section (44) configured to generate an output frame (46) by joining at least one input frame (10) of the time series (8) with the observation area (22) which is assigned a pseudocolor from a color space, the pseudocolor depending on the combination (72) and an output section (48) configured to output the output frame (46).

20. A medical observation device (1) comprising the image processor (26) according to claim 19 and a camera system (2) from which the input frames (10) are derived.

21. The medical observation device (1) according to claim 20, wherein the medical observation device (1) is a microscope.

22. The medical observation device (1) according to claim 20, wherein the medical observation device (1) is an endoscope.

* * * * *